United States Patent [19]

Steude et al.

[11] Patent Number: 5,400,381
[45] Date of Patent: Mar. 21, 1995

[54] PROCESS FOR ANALYZING THE CONTENTS OF CONTAINERS

[75] Inventors: John S. Steude, Cedar Park; Edwin L. Strickland, III, Austin, both of Tex.

[73] Assignee: Scientific Measurement Systems, Inc., Austin, Tex.

[21] Appl. No.: 59,018

[22] Filed: May 6, 1993

Related U.S. Application Data

[63] Continuation-in-part of Ser. No. 916,513, Jul. 20, 1992.

[51] Int. Cl.⁶ .............................................. H05G 1/64
[52] U.S. Cl. .................................. 378/57; 378/98.12
[58] Field of Search .................... 378/57, 58, 98.12

[56] References Cited

U.S. PATENT DOCUMENTS 4,791,655  12/1988  Nagata et al. ........................ 378/57
5,056,124  10/1991  Kakimoto et al. .................... 378/57

Primary Examiner—Craig E. Church
Attorney, Agent, or Firm—Shaffer & Culbertson

[57] ABSTRACT

A process for analyzing the contents of containers comprising obtaining a first image of the container, tilting the container, obtaining a second image of the contents of the container in the tilted position, overlaying the first and second images, and subtracting one image from the other so that contents that remain horizontal are identified and objects that tilt are substantially erased from view in the final differenced image. In one method, the container is manually or mechanically moved relative to the image taking device, such as a digital radiography device. In another method, in order to avoid parallax problems, the container and image taking device are moved together. Computed tomography can be used in combination to obtain more characterization of the contents including shapes, densities, atomic numbers, wall thicknesses, and the like.

23 Claims, 1 Drawing Sheet

PROCESS FOR ANALYZING THE CONTENTS OF CONTAINERS

This application is a continuation-in-part of application Ser. No. 07/916,513, filed Jul. 20, 1992.

BACKGROUND OF THE INVENTION

This invention relates to a process for analyzing the contents of containers. More specifically, it relates to a process for a digital radiography tilt method for detecting free liquids in hazardous and radioactive waste containers.

Vast quantities of radioactive waste materials have been generated as a result of the production of nuclear energy and defense materials over the past five decades. It has been estimated that there are over 1.4 million drums of buried and stored, high and low level waste, in the United States. There are also hundreds of facilities requiring decontamination and decommissioning that will generate many more drums of radioactive waste. Guidelines have been imposed concerning the safe handling of this waste and on the acceptable forms of radioactive waste materials for storage and disposal.

In an effort to ensure that containment drums do not rust and leak or otherwise release radioactive liquids and vapors into the environment, current regulations for radioactive waste require that drums contain less than one percent free liquids. There are additional requirements on the integrity of the drums and their contents that require a minimum drum wall thickness, and that no pressurized containers or flammable materials such as powdered metals, etc., are allowed without special processing and handling.

To date, the most practical means to certify that waste drums meet waste acceptance criteria is by non-destructive evaluation (NDE) methods. Opening drums for inspection and certification is not practical from either a safety or a cost basis because it is labor intensive and it creates additional waste in the location where the inspection occurs. The prior art in NDE methods used up to now have had some success, but it is widely recognized that there is room for improvement and for many types of waste in drums (e.g., cement solidified waste, compacted sludge, and vitrified waste), the capabilities of existing equipment and methods will not work.

The current method used to determine the presence of free liquids in drums is real-time radiography (RTR) and the method used for measuring drum wall thickness is ultrasound.

RTR imaging depends on X-ray attenuation measurements. RTR utilizes screen scintillators and image intensifiers for its measurements. Because RTR produces an image of a portion of drum in fractions of a second, moving fluids are visualized as they slosh in their container while the drum is rotated. The average time required by RTR to inspect an entire drum is ten minutes. It has been reported that RTR can detect as little as one teaspoon of water in a drum.

Some major disadvantages of RTR are: (1) containers that are full of liquids are not detectable because the liquids do not slosh, (2) the limited dynamic range of screen scintillators and image intensifiers (typically less than 100 intensity levels) have such limited contrast resolution that it is not possible to resolve common materials (i.e., plastics, glass, and metals) in the same image, (3) quantitative measurements of densities, atomic numbers, free liquid volumes, drum wall thickness, etc., are not possible, and (4) RTR systems have only been equipped with 420 kV X-ray tubes which will not penetrate drums filled with cement, sludge, or other dense waste forms.

Further, for quantitative measurements of drum wall thickness, prior art use of ultrasound measurements depend on the travel time of reflected acoustic signals from an output source back to a detector. Typically, wall thicknesses around the drum circumference at eight heights is measured. This measurement process usually requires 30 minutes. The ultrasound measurements are reported to be accurate within 0.001 inch.

The disadvantages of ultrasound are: (1) running water on the drum surface is required for good contact with the acoustic sensors, (2) ultrasound does not work on rusty drum surfaces, and (3) excessive measurement time is required, as indicated above.

Thus, there is a need in the art for a non-destructive means for detecting free liquids in waste containers and identifying the characteristics of the contents that is fast, conclusive, and cost-effective. Further, there is a need for a more convenient way to archive and recall the results for analysis at a later date. It, therefore, is an objective of this invention to provide a process for analyzing the contents of containers, such as drums containing radioactive wastes and the like, that overcomes the disadvantages of RTR and ultrasound and that is faster and provides results that are more readily interpreted than the results of prior art methods.

SHORT STATEMENT OF THE INVENTION

Accordingly, the process for analyzing the contents of containers of the present invention includes obtaining a first image of the contents of a container. Next, the container is tilted and a second image of the contents of the container in the tilted position is obtained. Next, the first and second images are overlaid and, finally, the images are compared one with the other so that contents that have remained horizontal during tilting, i.e., free liquid surfaces, are identified. In a preferred embodiment the steps of obtaining a first and second image are accomplished by use of a digital radiography device. The digital radiograph of the contents is then used for overlaying and subtraction purposes. Further, the digital radiograph scanner of the present invention includes an X-ray source and a detector. In one embodiment, the step of tilting includes tilting the container relative to the source and detector units of the scanner. The latter can be accomplished by an automatic tilt table, manually with blocks, etc. In another embodiment, the step of tilting the container includes tilting the scanner and the container together.

Further, in a preferred embodiment, the step of overlaying the first and second images is done digitally with computer software so that the two images are superimposed one over the other. This forces a horizontal surface pictured in the first image to become tilted relative to the horizontal surfaces that remained horizontal after being tilted, as shown by the second image. The step of comparing the first image with the second can be accomplished by means of a variety of mathematical tools including, subtracting, multiplying, adding, and dividing. The comparison is done pixel by pixel or in any manner sufficient to accurately reveal shifting.

The process can further include in combination the use of a computed tomography (CT) imaging device for obtaining quantitative measurements of the contents in the drum and of the drum itself. Such quantitative measurements include shapes, densities, atomic numbers, wall thicknesses, and the like. The supplementary CT measurements augment the ability to detect other unacceptable waste forms such as powders, pressurized containers, etc.

BRIEF DESCRIPTION OF THE DRAWINGS

Other objects, features, and advantages of the present invention will become more fully apparent from the following detailed description of the preferred embodiment, the appended claims, and the accompanying drawings in which:

DETAILED DESCRIPTION OF THE PREFERRED EMBODIMENT

Figure 1:
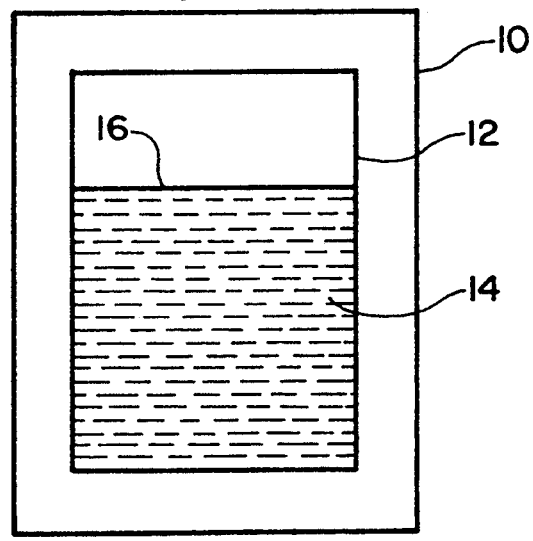
FIG. 1 is a front view illustration of an image of a container within which is located another container with free liquid.
Figure 2:
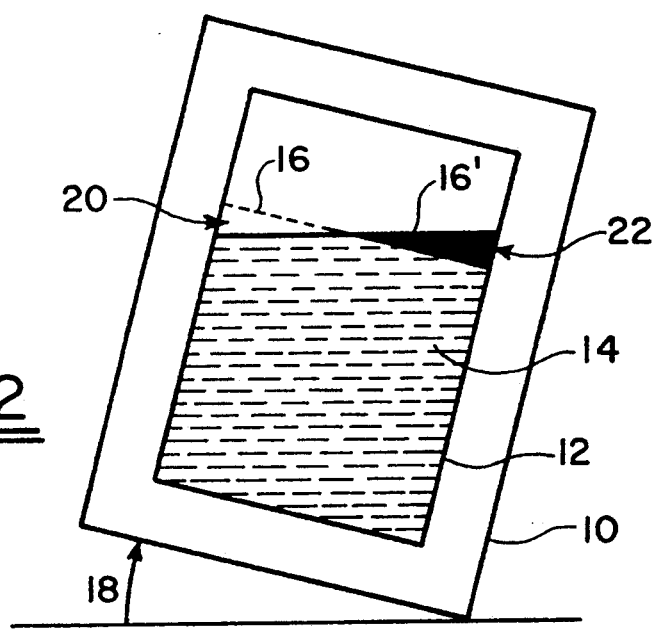
FIG. 2 is a front view of an image of the container of FIG. 1 shown in a tilted position in accordance with the process of the present invention showing the movement of the liquid in solid lines to remain horizontal and the dotted lines showing the forced tilted position of the fluid of FIG. 1 on top of FIG. 2.

FIG. 1 is an illustration of a container 10 within which is located a receptacle 12 containing free liquid 14. When container 10 is in the horizontal position, free liquid's 14 surface 16 assumes a horizontal position due to gravity. Referring now to FIG. 2, the process of the present invention includes tilting container 10 as illustrated by arrow 18. The free liquid 14 maintains its horizontal position as shown by the surface 16'. By means of overlaying the image of FIG. 1 with the image of FIG. 2 and comparing the constant images, by subtraction for example, the container 10 and receptacle 12 are essentially removed. As a result, the only thing left is an indicator with a white section 20 and a black section 22 wherein the surfaces 16 and 16' were forced one over the other to create a tilt and then subtracted, leaving the identifier as described. This same method applies to any free liquid surface within container 10 whether in receptacle 12 or not, e.g., free liquid at the bottom of container 10 or within a pocket of cement, sludge, soil, etc. Further, any manipulation of image data, whether by subtraction, addition, multiplication, division, or the like, that identifies shifting contents may be used.

In operation, the process of the invention is accomplished by use with a combined DR/CT scanner (digital radiography and computed tomography, respectively). The basic components of a DR/CT scanner are: (1) penetrating X- or gamma-ray source, (2) detector unit, (3) object handling unit, and (4) a computer for image processing. Computer hardware and software capable of accomplishing the overlay and subtraction step are known in the art and not disclosed further hereafter. An example of such a scanner is a model number 201 DR/CT manufactured by Scientific Measurement Systems, Inc. of Austin, Tex. (SMS). The SMS Model 201 is designed for large aerospace and automotive components up to six feet in size and weighing up to 2,000 pounds. It can be equipped with a 420 kV X-ray tube, an isotopic gamma-ray source, or a linear accelerator that provides either a 2.5, 6, or 9 MeV X-ray source. The dynamic range of the linear detector array provides X-ray measurements over several hundred thousand intensity levels. This provides highly sensitive density contrast resolution for exceptionally dense materials as well as very light materials. Density resolution is generally on the order of 0.5% for most materials. Spatial dimensioning accuracy is typically 0.001 inch. The DR/CT scanner of the present invention is specifically designed for drum inspection and has scan times of less than one minute per image. The scanner can also be a portable system designed for use in the field under harsh conditions. Speed enhancement is acquired by adding additional detectors that are more closely spaced and by shortening the distance between the scanner source and detectors.

To begin, a container to be analyzed is placed on the scanner and a digital radiograph of the container is taken. By means of the single radiograph, it is often possible to distinguish containers with liquids from those with powders due to the fact that liquids have smooth horizontal surfaces while powders have rough, irregular surfaces. Although the single digital radiograph reveals the identity of many items in a drum, it cannot by itself identify free liquid in a conclusive manner. This is possible, however, by means of the process of the present invention including the steps of taking a first radiograph image of the drum, tilting the drum a few degrees, taking a second radiograph of the drum in the tilted position, and digitally overlaying and subtracting one radiograph from the other by means of computer software known in the art. Because the liquid surfaces will move relative to their containers in the tilted drum, comparison, by subtraction for example, of the images conclusively identifies liquids in a drum with a positive/negative "fingerprint" where the liquids moved relative to their containers. Free liquid surfaces are clearly identified by a black and white bar where they shifted relative to the containers. Should some containers hold powdered material that settles during tilting, this will be identified as well. This effect, however, is distinguished by a solid white or black (depending on which image is subtracted) line at the surface instead of the polarity of the black and white bar associated with shifted liquid surfaces.

In a preferred embodiment, the method of tilting the container consists of manually or mechanically moving the container itself from an upright position on the scanner to a tilted position. This is a simple and effective means of producing the required movement necessary to force the liquid to move relative to its containers so that the properly identifying signature may be obtained from whatever liquid is present.

Another preferred embodiment eliminates the problem of parallaxing that occurs by means of use of the first tilting method. Because of the geometric relationship of the X-ray source, container, and detectors, the movement of the container results in the movement of the contents of the container and results in a parallax view when the images are compared so that the images aren't totally removed from those items which have actually remained stationary during the tilt. However, by means of tilting the entire scanner and drum for the second image, it is possible to remove the whole image of the stationary items for the reason that the problem of parallaxing has been circumvented.

A major advantage of the process of the present invention is that because of the distinct indication, a black and white bar or mirror image triangles associated with shifted liquid surfaces, liquid levels are detectable in containers that have overlapping images due to their position in the drum with respect to the viewing angle.

Further, the invention is extremely sensitive in that it has been possible to identify the black and white signal associated with the shifting of as little as 1.0 and 2.5 milliliters of water.

There are circumstances when radiography alone will not provide enough information to completely characterize the entire contents of a drum for all of the waste acceptance criteria that need to be met. In this case, a combined DR/CT process is used. CT images can be obtained in scanning times on the order of one minute and would be used in a variety of situations, when it is necessary to further characterize the contents of the drum or the characteristics of the drum itself. For example, a CT image can be taken where there is an indication of a puncture hole in an aerosol can, as required, for disposal, but a CT scan is needed to confirm the presence of the hole.

Further, the only NDE method currently available to inspect cement-solidified waste drums and to make quantitative density measurements thereof to determine whether they contain air or water is by CT with a high energy linear accelerator source (2 MeV or greater).

A single CT image represents a precise two-dimensional map of density that is independent of the shapes and locations of objects of interest. Multiple CT images can be used to obtain precise 3-dimensional density maps. The sensitivity of CT measurements to slight changes in density is typically orders of magnitude better than that obtainable with radiography.

Atomic number maps are obtained by scanning objects with a high and low X-ray energy and processing the data to extract the X-ray attenuation due to atomic number from that due to density.

The ability of CT to measure the atomic numbers of various liquids, powders, and solids in their bulk forms is a capability not available by any other NDE method.

A CT image can also be used to measure drum wall thickness because it is a spatially resolved map of density. Image analysis software used in the art provides the ability to draw a line on an image. The software plots the density along that line to display a density profile. The height and width of a spike in the density at the drum wall is directly proportional to the drum wall thickness. With calibration, the density profiles across the drum wall can measure drum wall thickness to an accuracy on the order of 0.001 inch. This analysis process can be automated to find the thinnest portion of drum wall.

The time required to measure the thinnest wall around the drum circumference at eight heights on the drum wall is approximately eight minutes. Further, the eight CT images are used to inspect the waste inside the drum. The prior art technology, ultrasound, takes three to four times longer for the same wall thickness measurements and does not provide any information on the drum contents. Furthermore, measurements by the present invention will work on rusty drum surfaces while ultrasound measurements will not.

In summary, the process of the present invention enables rapid detection of small amounts of free liquids in drums with miscellaneous contents. The digital radiographic technique of the present invention depends on the shifting of liquids relative to their containers when a drum is tilted. Titled and non-tilted drum images are overlaid and the difference between them identifies liquid surfaces with a conclusive indicator, such as a black and white signature.

Further, in combination, CT inspection techniques can provide estimates of volumes of liquids in their containers and identify small amounts of free liquids in dense forms of waste. Still further, the CT/DR combination enables drum wall thickness measurements where prior art devices presently are ineffective.

While the present invention has been disclosed in connection with the preferred embodiment thereof, it should be understood that there may be other embodiments which fall within the spirit and scope of the invention as defined by the following claims.

I claim:

1. A process for analyzing the contents of containers which comprises:
    a) obtaining a first image of the contents of a container;
    b) tilting said container;
    c) obtaining a second image of the contents of said container in the titled position;
    d) overlaying said first and second images; and
    e) comparing one image with the other so that contents that remain horizontal are identified.

2. The process of claim 1 wherein the steps of obtaining a first and second image further comprises the step of utilizing a digital radiography means for obtaining a digital radiograph of said contents.

3. The process of claim 2 wherein said digital radiography means includes a penetrating energy source means and a detector means.

4. The process of claim 3 wherein the step of tilting said container includes tilting said container relative to the source and detector means.

5. The process of claim 3 wherein the step of tilting said container includes tilting said digital radiography means and said container together.

6. The process of claim 5 wherein the step of overlaying said first and second images is done digitally with a computer means so that said images are superimposed thereby forcing a horizontal surface from the first image to become tilted relative to said horizontal surface in said second image resulting in an easily measured and observed identifier.

7. The process of claim 6 wherein the analysis of the contents of containers further comprises the step of utilizing in combination a computed tomography imaging means for obtaining quantitative measurements of materials in suspect regions of said container identified by said digital radiography means.

8. The process of claim 7 wherein said quantitative measurements are selected from a group including shapes, densities, atomic numbers, wall thicknesses, and the like.

9. The process of claim 4 wherein the step of overlaying said first and second images is done digitally with a computer means so that said images are superimposed thereby forcing a horizontal surface from the first image to become tilted relative to said horizontal surface in said second image resulting in an easily measured and observed identifier.

10. The process of claim 9 wherein the analysis of the contents of containers further comprises the step of utilizing in combination a computed tomography imaging means for obtaining quantitative measurements of materials in suspect regions of said container identified by said digital radiography means.

11. The process of claim 10 wherein said quantitative measurements are selected from a group including shapes, densities, atomic numbers, wall thicknesses, and the like.

12. A digital radiography tilted method for detecting free liquids in hazardous and radioactive waste containers comprising the steps of:
   a) obtaining a first digital radiograph of the contents of a container;
   b) tilting said container;
   c) obtaining a second digital radiograph of said container in the tilted position;
   d) digitally overlaying said first and second digital radiograph images; and
   e) comparing one digital radiograph with the other so that free liquid surfaces that remain horizontal are identified.

13. The method of claim 12 wherein the steps of obtaining digital radiographs include a digital radiography means with a penetrating energy source means and a detector means.

14. The method of claim 13 wherein the step of tilting said container includes tilting said container relative to the source and detector means.

15. The method of claim 14 wherein the step of tilting said container includes tilting said digital radiography means and said container together.

16. The method of claim 15 wherein the step of overlaying said first and second images is done digitally with a computer means so that said images are superimposed thereby forcing a horizontal surface from the first image to become tilted relative to said horizontal surface in said second image resulting in an easily measured and observed identifier.

17. The method of claim 16 wherein the analysis of the contents of containers further comprises the step of utilizing in combination a computed tomography imaging means for obtaining quantitative measurements of materials in suspect regions of said container identified by said digital radiography means.

18. The method of claim 17 wherein said quantitative measurements are selected from a group including shapes, densities, atomic numbers, wall thicknesses, and the like.

19. The method of claim 14 wherein the step of overlaying said first and second images is done digitally with a computer means so that said images are superimposed thereby forcing a horizontal surface from the first image to become tilted relative to said horizontal surface in said second image resulting in an easily measured and observed identifier.

20. The method of claim 19 wherein the analysis of the contents of containers further comprises the step of utilizing in combination a computed tomography imaging means for obtaining quantitative measurements of materials in suspect regions of said container identified by said digital radiography means.

21. The method of claim 20 wherein said quantitative measurements are selected from a group including shapes, densities, atomic numbers, wall thicknesses, and the like.

22. The process of claim 11 wherein the comparison of one image with the other includes one means from a group including subtracting, adding, dividing, and multiplying so that contents that remain horizontal are identified.

23. The method of claim 21 wherein the step of comparing one digital radiograph with the other includes one from a group including subtracting, adding, dividing, and multiplying so that free liquid surfaces that remain horizontal are indicated.

* * * * *